United States Patent [19]
Cotteret et al.

[11] Patent Number: 5,868,800
[45] Date of Patent: Feb. 9, 1999

[54] COMPOSITION FOR THE OXIDATION DYEING OF KERATINOUS FIBRES, COMPRISING A PARA-PHENYLENEDIAMINE DERIVATIVE AND A 6-HYDROXY-1, 4-BENZOMORPHOLINE AND DYEING PROCESS USING SUCH A COMPOSITION

[75] Inventors: Jean Cotteret, Verneuil sur Seine; Marie-Pascale Audousset, Asnieres, both of France

[73] Assignee: L'Oreal, Paris, France

[21] Appl. No.: 872,384

[22] Filed: Jun. 10, 1997

Related U.S. Application Data

[63] Continuation of Ser. No. 451,505, May 26, 1995, Pat. No. 5,690,695.

[30] Foreign Application Priority Data

May 26, 1994 [FR] France ................................. 94 06394

[51] Int. Cl.$^6$ ...................................................... A61K 7/13
[52] U.S. Cl. ........................ 8/410; 8/408; 8/409; 8/416; 8/423; 8/565; 8/576
[58] Field of Search ............................... 8/406, 408, 409, 8/410, 416, 423, 570, 576, 565

[56] References Cited

U.S. PATENT DOCUMENTS

| | | | |
|---|---|---|---|
| 3,690,810 | 9/1972 | Bugant et al. | 8/409 |
| 4,217,914 | 8/1980 | Jacquet et al. | 8/426 |
| 4,289,495 | 9/1981 | Bugaut et al. | 8/408 |
| 4,402,698 | 9/1983 | Kalopissis et al. | 8/406 |
| 4,545,978 | 10/1985 | Kalopissis et al. | 8/405 |
| 4,566,875 | 1/1986 | Grollier et al. | 8/406 |
| 4,840,639 | 6/1989 | Husemeyer et al. | 8/410 |
| 4,875,902 | 10/1989 | Grollier et al. | 8/408 |
| 4,904,275 | 2/1990 | Grollier | 8/411 |
| 5,203,875 | 4/1993 | Tuloup et al. | 8/423 |
| 5,344,464 | 9/1994 | Madrange et al. | 8/408 |
| 5,443,596 | 8/1995 | Junino et al. | 8/421 |

FOREIGN PATENT DOCUMENTS

| | | |
|---|---|---|
| 0 007 537 | 2/1980 | European Pat. Off. . |
| 2 015 589 | 4/1970 | France . |
| 2 270 846 | 5/1976 | France . |
| 2 078 747 | 1/1982 | United Kingdom . |

OTHER PUBLICATIONS

American Society for Testing and Materials, "Standard Practice for Specifying Color by the Munsell System", Designation: D 1535–95b (undated) (no date available).

*Primary Examiner*—Paul Lieberman
*Assistant Examiner*—Caroline D. Liott
*Attorney, Agent, or Firm*—Finnegan, Henderson, Farabow, Garrett & Dunner, L.L.P.

[57] ABSTRACT

The invention relates to an oxidation dyeing composition for keratinous fibres, in particular for human keratinous fibres such as hair, of the type which comprises, in a medium appropriate for dyeing, at least one oxidation dye precursor and at least one coupler, and which is characterized in that it contains, as oxidation dye precursor, at least one para-phenylenediamine which is substituted in position 2 on the benzene ring, and/or at least one of its addition salts with an acid, and, as coupler, at least one specific 6-hydroxy-1,4-benzomorpholine and/or at least one of its addition salts with an acid. The invention also relates to the use of this composition for the dyeing of keratinous fibres, especially hair.

21 Claims, No Drawings

COMPOSITION FOR THE OXIDATION DYEING OF KERATINOUS FIBRES, COMPRISING A PARA-PHENYLENEDIAMINE DERIVATIVE AND A 6-HYDROXY-1, 4-BENZOMORPHOLINE AND DYEING PROCESS USING SUCH A COMPOSITION

This is a continuation of application Ser. No. 08/451,505, filed May 26, 1995, now U.S. Pat. No. 5,690,695.

The present invention relates to a composition for the oxidation dyeing of keratinous fibres and, in particular, human keratinous fibres, comprising a combination of at least one para-phenylenediamine which is substituted in position 2 on the benzene ring and a 6-hydroxy-1,4-benzomorpholine, the structures of which are given below in the description. The invention also relates to the use of such a composition.

It is known to dye keratinous fibres and, in particular, human hair, with dyeing compositions which contain oxidation dye precursors, especially ortho- or para-phenylenediamines, ortho- or para-aminophenols, which are generally termed "oxidation bases", in combination with couplers, also called coloration modifiers, which are more particularly meta-phenylenediamines, meta-aminophenols and meta-diphenols, which enable the "foundation" colorations obtained by the condensation products of the oxidation bases to be modified and enriched with glints.

Thus, para-phenylenediamine is traditionally combined with meta-dihydroxybenzene, better known as resorcinol, in order to obtain intense natural shades.

Since the use of para-phenylenediamine has been called into question again for reasons of toxicology, it has already been proposed in the patent application WO 80/0014 and in the patent EP-0 400 330 B1 to use, as replacement for para-phenylenediamine, para-phenylenediamine derivatives which are mono-hydroxyalkylated in position 2 on the benzene ring.

However, when resorcinol is combined with these para-phenylenediamine derivatives which are monohydroxyalkylated in position 2 on the benzene ring, the natural shades desired are too low in intensity to enable the formulator to create a wide range of shades.

Following major research carried out on this subject, the inventors have now discovered that it is possible to obtain novel nontoxic dyes which give rise to intense natural shades by combining a para-phenylenediamine substituted in position 2 on the benzene ring with a 6-hydroxy-1,4-benzoxazine, these compounds having, respectively, the structures defined below.

It is this discovery which forms the basis of the present invention.

The subject of the present invention is thus an oxidation dyeing composition for keratinous fibres, in particular for human keratinous fibres such as hair. The composition comprises, in a medium appropriate for dyeing, at least one oxidation dye precursor and at least one coupler, wherein the composition contains, as oxidation dye precursor, at least one para-phenylenediamine of the following formula (I):

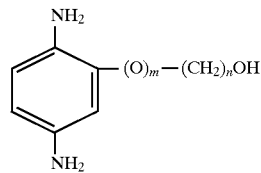

in which m is an integer equal to zero or 1, and n is an integer from 1 to 4, and/or at least one of the addition salts of this para-phenylenediamine with an acid, and wherein the composition further contains, as coupling agent, at least one 6-hydroxy-1,4-benzomorpholine of the following formula (II):

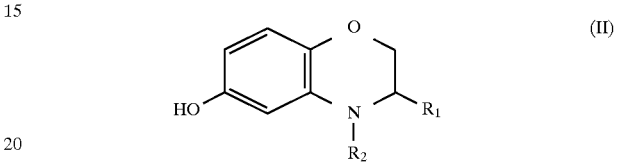

in which the radicals $R_1$ and $R_2$ denote, independently of one another or simultaneously, a hydrogen atom or a lower alkyl radical containing 1 to 4 carbon atoms, and/or at least one of the addition salts of this benzoxazine with an acid.

The novel dyes thus obtained make it possible to obtain nontoxic and long-lasting natural colorations.

These novel dyes additionally exhibit good resistance to shampoos and have good covering power on white hair.

The invention also relates to the ready-to-use composition containing the various agents which are used for the dyeing of keratinous fibres and which are defined below, and an oxidizing agent.

The invention also relates to a process for dyeing keratinous fibres and, in particular, human keratinous fibres such as hair. The process comprises applying to these fibres at least one composition (A) containing, in a medium appropriate for dyeing, at least one oxidation dye precursor and at least one coupler as defined above, the colour being revealed at an alkaline, neutral or acid pH with the aid of an oxidizing agent which is added to the composition (A) at the time of use or which is present in a composition (B) which is applied simultaneously or sequentially and separately.

The invention also relates to multi-compartment kits or dyeing devices in which the first compartment contains at least one para-phenylenediamine of formula (I) as oxidation dye precursor and at least one 6-hydroxy-1,4-benzomorpholine of formula (II) as coupler, and the second compartment contains an oxidizing agent.

Other characteristics, aspects, subjects and advantages of the invention will appear even more clearly on reading the description and examples which follow.

The acid salts which may be used according to the invention are preferably chosen from hydrochlorides, sulphates, hydrobromides and tartrates. Among the oxidation dye precursors which can be used in the context of the present invention, the following compounds are preferably employed: 2-hydroxymethyl-para-phenylenediamine, 2-β-hydroxyethyl-para-phenylenediamine and 2-β-hydroxyethyloxy-para-phenylenediamine. More preferably, 2-β-hydroxyethyl-para-phenylenediamine is employed.

The concentration of this or these precursor(s) or salts thereof can generally vary from 0.01 to 10% by weight, approximately, relative to the total weight of the dyeing composition, and preferably from 0.05 to 5% by weight approximately.

Among the couplers of formula (II) it is preferred more particularly to employ 6-hydroxy-1,4-benzomorpholine and N-methyl-6-hydroxy-1,4-benzomorpholine.

The concentration of coupler(s) of formula (II) or salts thereof may generally vary from 0.005 to 5% by weight, approximately, relative to the total weight of the dyeing composition, and preferably from 0.01 to 3% by weight approximately.

Oxidation dyeing compositions which are more particularly preferred according to the invention comprise, as oxidation dye precursor, 2-β-hydroxyethyl-para-phenylenediamine or one of its salts and, as coupler, 6-hydroxy-1,4-benzomorpholine or N-methyl-6-hydroxy-1,4-benzomorpholine or one of their salts.

Other compositions which are also particularly advantageous comprise, as oxidation dye precursor, 2-β-hydroxyethyloxy-para-phenylenediamine or one of its salts and, as coupler, 6-hydroxy-1,4-benzomorpholine or N-methyl-6-hydroxy-1,4-benzomorpholine or one of their salts.

The oxidizing agent is preferably chosen from hydrogen peroxide, urea peroxide, alkali metal bromates, and per salts such as perborates and persulphates. The use of hydrogen peroxide is particularly preferred.

Composition (A), which contains the dye combination as described above, may have a pH from 3 to 11 which may be adjusted to the chosen value either by means of basifying agents which are commonly used in the dyeing of keratinous fibres, such as aqueous ammonia, alkali metal carbonates, alkanolamines, for example mono-, di- and triethanolamines and the derivatives thereof, potassium or sodium hydroxides, and the compounds of formula:

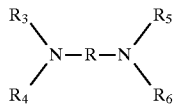

in which R is a propylene radical which is optionally substituted with a hydroxyl group or a $C_1$–$C_4$ alkyl radical, and $R_3$, $R_4$, $R_5$ and $R_6$, simultaneously or independently of one another, represent a hydrogen atom or a $C_1$–$C_4$ alkyl or $C_1$–$C_4$ hydroxyalkyl radical, or by means of conventional acidifying agents, such as inorganic acids or organic acids such as, for example, hydrochloric, tartaric, citric and phosphoric acids.

The pH of composition (B), containing the oxidizing agent as defined above, is such that, after mixing with composition (A), the pH of the composition which is applied to the human keratinous fibres varies preferably from 3 to 11. It is adjusted to the desired value with the aid of acidifying agents or, if appropriate, basifying agents which are well known from the prior art, such as those described above.

The oxidizing composition (B) consists preferably of a solution of hydrogen peroxide.

According to a preferred embodiment of the dyeing process of the invention, the dyeing composition (A) described above is mixed at the time of use with an oxidizing solution in a quantity which is sufficient to bring about a coloration. The mixture obtained is subsequently applied to the human keratinous fibres and is generally left to act for from 5 to 40 minutes, preferably from 15 to 30 minutes, after which the hair is rinsed, washed with shampoo, rinsed again and dried.

The dyeing compositions may also contain, in addition to the dyes defined above, other couplers and other oxidation bases of formulae (I) and (II) and/or direct dyes and/or melanin precursors, especially in order to modify the shades or enrich them with glints. Very particular mention may be made in this context of the combination of 2-β-hydroxyethyl-paraphenylene- diamine, 6-hydroxy-1,4-benzomorpholine and 6-hydroxyindole, or the addition salts thereof with an acid.

The dyeing compositions may also contain antioxidants. These may be chosen, in particular, from sodium sulphite, thioglycolic acid, thiolactic acid, sodium bisulphite, dehydroascorbic acid, hydroquinone, 2-methylhydroquinone, tert-butylhydroquinone, 3-methyl-1-phenyl-5-pyrazolone and homogentisic acid and are then generally present in proportions of from approximately 0.05 to 1.5% by weight relative to the total weight of the composition.

The dyeing compositions also contain, in their preferred embodiment, surfactants which are well known in the art, generally in proportions of approximately from 0.5 to 55% by weight, and preferably from 2 to 50% by weight relative to the total weight of the composition, organic solvents generally in proportions of from approximately 1 to 40% by weight and, in particular, from 5 to 30% by weight relative to the total weight of the composition, or any other adjuvant which is cosmetically acceptable and is known in the prior art for the oxidation dyeing of hair.

The composition which is applied to the hair may be presented in various forms such as in the form of a liquid, cream or gel or in any other form which is suitable for dyeing keratinous fibres and, in particular, human hair. In particular, it may be packaged under pressure in an aerosol can in the presence of a propellant and may form a foam.

Concrete examples which illustrate the invention will now be given.

EXAMPLES

Example 1

The following dyeing composition in accordance with the invention was prepared:

2-β-hydroxyethyl-para-phenylenediamine, dihydrochloride 0.675 g 6-hydroxy-1,4-benzomorpholine 0.453 g lauric acid 3.5 g decyl alcohol, ethoxylated with 3.5 mol of ethylene oxide (Mergital BL309 from Sinnova-Henkel) 10.0 g lauryl alcohol, ethoxylated with 12 mol of ethylene oxide (Lauropal 12 from Witco) 10.0 g cetylstearyl alcohol 10.5 g glycol distearate 1.5 g oleocetyl alcohol, ethoxylated with 30 mol of ethylene oxide (Mergital OC 30 from Sinnova-Henkel) 6.0 g pyrogenic silica (Aerosil R972 from Degussa) 2.0 g propylene glycol 8.0 g crosslinked polyacrylic acid (Carbopol 980 from Goodrich) 0.4 g dipropylene glycol 2.0 g cationic cosmetic polymer described and prepared according to French Patent FR 2 270 846, the disclosure of which is hereby incorporated by reference, consisting of repeating units of formula:

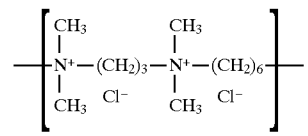

in aqueous solution at a concentration of 60% of active substance (A.S.) 4.2 g A.S monoethanolamine 1.4 g aqueous ammonia solution containing 20% of NH$_3$ 2.22 g A.S.

reducing agents, antioxidants, sequestering agents and fragrances q.s.

demineralized water q.s. 100.0 g

This composition was mixed at the time of use with 1.5 times its weight of 20-volume hydrogen peroxide (6% by weight) with a pH of 3. A mixture of pH 9.8 was obtained.

This mixture was then applied to two types of hair—grey hair containing 90% of white hairs and permanent-waved grey hair containing 90% of white hairs—for 30 minutes. After rinsing, washing with shampoo, rinsing, and drying, the hair was dyed in a shade with an intensity which was much longer-lasting than that obtained from an identical dyeing composition in which the 6-hydroxy-1,4-benzomorpholine was replaced, however, by an equivalent molar quantity of resorcinol (0.327 g).

The L, a, b values (colour notation system in which L denotes intensity, a denotes shade and b denotes purity) of these comparative shades were measured on a Minolta CM2002 calorimeter.

The intensity values of the coloration, in terms of L, were as follows:

| | Value of L | |
|---|---|---|
| | on 90% white hair | on permanent-waved 90% white hair |
| Dyeing composition according to the invention | 43.19 | 32.82 |
| Control containing resorcinol | 47.40 | 38.78 |

In the L, a, b notation system, the lower the value of L the more intense the shade.

A significantly more intense shade was thus observed with the composition according to the invention in comparison with the shade obtained with its prior art control containing resorcinol.

Example 2

The following dyeing composition in accordance with the invention was prepared:

2-β-hydroxyethyl-para-phenylenediamine, dihydrochloride 4.4 g 6-hydroxy-1,4-benzomorpholine 2.0 g 2-aminophenol 1.3 g 2,4-diamino-1-(β-hydroxyethyloxy)-benzene, dihydrochloride 0.3 g 6-hydroxyindole 0.325 g 5-N-(β-hydroxyethylamino)-2-methylphenol 0.78 g lauric acid 3.5 g decyl alcohol, ethoxylated with 3.5 mol of ethylene oxide (Mergital BL309 from Sinnova-Henkel) 10.0 g lauryl alcohol, ethoxylated with 12 mol of ethylene oxide (Lauropal 12 from Witco) 10.0 g cetylstearyl alcohol 10.5 g glycol distearate 1.5 g oleocetyl alcohol, ethoxylated with 30 mol of ethylene oxide (Mergital OC 30 from Sinnova-Henkel) 6.0 g pyrogenic silica (Aerosil R972 from Degussa) 2.0 g propylene glycol 5.0 g crosslinked polyacrylic acid (Carbopol 980 from Goodrich) 0.4 g dipropylene glycol 2.0 g cationic cosmetic polymer described and prepared according to French Patent FR 2 270 846, consisting of repeating units of formula:

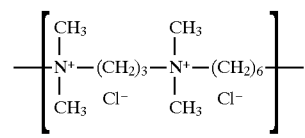

in aqueous solution at a concentration of 60% of active substance (A.S.) 4.2 g A.S monoethanolamine 1.4 g aqueous ammonia solution containing 20% of NH$_3$ 2.22 g A.S.

reducing agents, antioxidants, sequestering agents and fragrances q.s.

demineralized water q.s. 100.0 g

Following the same dyeing protocol as in Example 1, a particularly intense chestnut-brown shade was obtained on natural grey hair containing 90% of white hairs and on permanent-waved grey hair containing 90% of white hairs.

Example 3

The following dyeing composition in accordance with the invention was prepared:

2-(β-hydroxyethyl)-para-phenylenediamine, dihydrochloride 1.50 g 6-hydroxy-1,4-benzomorpholine 1.20 g 6-hydroxyindole 0.25 g 2,4-diamino-1-(β-hydroxyethyloxy)-benzene, dihydrochloride 0.20 g 2-aminophenol 0.15 g 3-methyl-para-aminophenol 0.35 g 5-N-(β-hydroxyethylamino)-2-methylphenol 0.15 g octyldodecanol sold under the name Eutanol D by the company Henkel 8.0 g oleic acid 20.0 g monoethanolamine lauryl ether sulphate sold under the name Sipon LM 35 by the company Henkel 3.0 g ethyl alcohol 10.0 g benzyl alcohol 10.0 g cetylstearyl alcohol, ethoxylated with 33 mol of ethylene oxide, sold under the name Simulsol GS by the company Seppic 2.4 g cationic cosmetic polymer described and prepared according to French Patent FR 2 270 846, consisting of repeating units of formula:

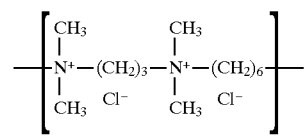

in aqueous solution at a concentration of 60% of active substance (A.S.) 2.22 g A.S monoethanolamine 9.0 g linoleic acid diethanolamide, sold under the name Comperlan F by the company Henkel 8.0 g aqueous solution of sodium meta-bisulphite, containing 35% of active substance 0.455 g A.S.

sequestering agent, antioxidants q.s.

fragrance, preservative q.s.

demineralized water q.s. 100.0 g

This composition was mixed at the time of use with 2 times its weight of 9-volume hydrogen peroxide with a pH of 3. A mixture of pH 9.2 was obtained.

This mixture was then applied to permanent-waved and to untreated grey hair containing 90% of white hairs, for 15 minutes. After rinsing, washing with shampoo, rinsing and drying, the hair was dyed in an intense dark blonde shade.

What is claimed is:

1. An oxidation dyeing composition for keratinous fibres, the composition comprising, in a medium appropriate for dyeing, at least one oxidation dye precursor and at least one coupler, wherein said composition contains, as said at least one oxidation dye precursor, a para-phenylenediamine of the following formula (I):

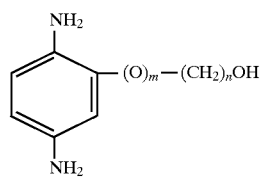

in which m is an integer equal to 1, and n is an integer from 1 to 4 or an acid addition salt of said para-phenylenediamine, and wherein said composition further contains, as said at least one coupler, a 6-hydroxy-1,4-benzomorpholine of the following formula (II):

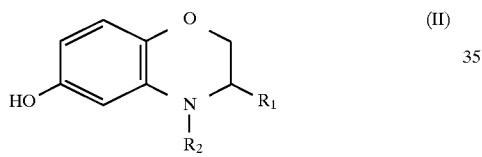

in which the radicals $R_1$ and $R_2$ are the same or different and denote a hydrogen atom or an alkyl radical containing 1 to 4 carbon atoms or an acid addition salt of said benzomorpholine, said at least one oxidation dye precursor and said at least one coupler being present in amounts effective to dye keratinous fibres.

2. The dyeing composition of claim 1, wherein said keratinous fibers are human keratinous fibres.

3. The dyeing composition of claim 2, wherein said human keratinous fibers are human hair.

4. The dyeing composition according to claim 1, wherein the para-phenylenediamine of formula (I) is selected from 2-hydroxymethyloxy-para-phenylenediamine, 2-β-hydroxyethyloxy-para-phenylenediamine, or their acid addition salts.

5. The dyeing composition according to claim 1, wherein the coupler of formula (II) is selected from 6-hydroxy-1,4-benzomorpholine N-methyl-6-hydroxy-1,4-benzomorpholine.

6. The dyeing composition according to claim 1, wherein said composition contains:

at least one oxidation dye precursor of formula (I) selected from 2-β-hydroxyethyloxy-para-phenylenediamine, or an acid addition salt thereof and at least one coupler of formula (II) selected from 6-hydroxy-1,4-benzomorpholine, N-methyl-6-hydroxyl-1,4-benzomorpholine, or an acid addition salt thereof.

7. The dyeing composition according to claim 1, wherein said composition contains:

at least one oxidation dye precursor of formula (I) selected from 2-β-hydroxyethyloxy-para-phenylenediamine, or an acid addition salt thereof and at least one coupler of formula (II) selected from 6-hydroxy-1,4-benzomorpholine or an acid addition salt thereof, and at least one additional dye selected from 6-hydroxyindole or an acid addition salt thereof.

8. The dyeing composition according to claim 1, wherein said acid addition salts are selected from hydrochlorides, sulphates, hydrobromides or tartrates.

9. The dyeing composition according to claim 1, wherein said para-phenylenediamine of formula (I) or acid addition salt of said para-phenylenediamine is present in a concentration of from 0.01 to 10% by weight relative to the total weight of the composition and wherein said 6-hydroxy-1,4-benzomorpholine of formula (II) or acid addition salt of said 6-hydroxy-1,4-benzomorpholine is present in a concentration of from 0.005 to 5% by weight relative to the total weight of the composition.

10. The dyeing composition according to claim 9, wherein said para-phenylenediamine of formula (I) or acid addition salt of said para-phenylenediamine is present in a concentration of from 0.05 to 5% by weight relative to the total weight of the composition and wherein said 6-hydroxy-1,4-benzomorpholine of formula (II) or acid addition salt of said 6-hydroxy-1,4-benzomorpholine is present in a concentration of from 0.01 to 3% relative to the total weight of the composition.

11. The dyeing composition according to claim 1, wherein said composition additionally contains an oxidizing agent and further wherein said composition has a pH from 3 to 11.

12. A process for dyeing keratinous fibres comprising:

applying to the fibres a dyeing composition (A) according to the oxidation dyeing composition of claim 1 and developing a color in an alkaline, neutral, or acid medium with the aid of an oxidizing agent which is added to said dyeing composition (A) at the time of application to said fibres or which is present in the form of a composition (B) which is applied simultaneously with and separately from said dyeing composition (A) or sequentially to said dyeing composition (A).

13. The process of claim 12, wherein said keratinous fibers are human keratinous fibres.

14. The process of claim 13, wherein said human keratinous fibers are hair.

15. A multi-compartment device or kit for the dyeing of keratinous fibres comprising at least two compartments, one of which contains a dyeing composition (A) according to the oxidation dyeing composition of claim 1 and another of which contains a composition (B) comprising an oxidizing agent in a medium appropriate for dyeing.

16. The device or kit of claim 15, wherein said keratinous fibers are human keratinous fibres.

17. The device or kit of claim 16, wherein said human keratinous fibers are hair.

18. A method of dyeing human keratinous fibres comprising applying to said human keratinous fibers a dyeing composition according to claim 1.

19. The method of claim 18, wherein said human keratinous fibers are hair.

20. A method of dyeing human keratinous fibers comprising applying to said human keratinous fibers compositions (A) and (B) as defined in claim 15 which are present in a multi-compartment kit or dyeing device according to claim 15.

21. The method of claim 20, wherein said human keratinous fibers are hair.

* * * * *

UNITED STATES PATENT AND TRADEMARK OFFICE
CERTIFICATE OF CORRECTION

PATENT NO.: 5,868,800

DATED: Feb. 9, 1999

INVENTOR(S): Cotteret et al.

It is certified that an error appears in the above-identified patent and that said Letters Patent is hereby corrected as shown below:

Claim 5, column 7, line 57, before "N-methyl" insert --or--.

Signed and Sealed this

Twenty-fifth Day of May, 1999

Attest:

Q. TODD DICKINSON

*Attesting Officer*   *Acting Commissioner of Patents and Trademarks*